United States Patent [19]
von der Saal et al.

[11] Patent Number: 4,730,003

[45] Date of Patent: Mar. 8, 1988

[54] TRICYCLIC COMPOUNDS FOR TREATING HEART AND CIRCULATORY DISEASES

[75] Inventors: Wolfgang von der Saal, Weinheim; Alfred Mertens, Schriesheim; Herbert Berger, Mannheim; Bernd Müller-Beckmann, Grünstadt, all of Fed. Rep. of Germany

[73] Assignee: Boehringer Mannheim GmbH, Mannheim, Fed. Rep. of Germany

[21] Appl. No.: 904,094

[22] Filed: Sep. 4, 1986

[30] Foreign Application Priority Data

Sep. 5, 1985 [DE] Fed. Rep. of Germany ....... 3531678

[51] Int. Cl.⁴ ................. A61K 31/415; C07D 487/04; C07D 498/04; C07D 513/04
[52] U.S. Cl. ..................... 514/387; 514/278; 514/338; 514/366; 514/375; 514/388; 514/394; 514/395; 546/15; 546/271; 548/147; 548/151; 548/216; 548/218; 548/305; 548/306; 548/326
[58] Field of Search ............... 548/326, 305, 306, 147, 548/151, 216, 218; 546/15, 271; 514/278, 338, 366, 375, 387, 388, 394, 395

[56] References Cited
PUBLICATIONS

*Chemical Abstracts,* 104:186410e (1986) [Ger. Offen. 3,417,643, Hoelck et al., 11/14/85].

*Primary Examiner*—Richard A. Schwartz
*Attorney, Agent, or Firm*—Felfe & Lynch

[57] ABSTRACT

The present invention provides compounds of the general formula:

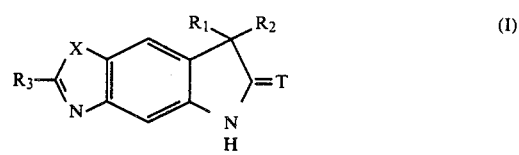

wherein the various substituents are defined hereinbelow. The compounds are used for the treatment and/or prophylaxis of heart and circulatory diseases.

22 Claims, No Drawings

TRICYCLIC COMPOUNDS FOR TREATING HEART AND CIRCULATORY DISEASES

The present invention is concerned with new tricyclic compounds, processes for the preparation thereof and pharmaceutical compositions containing them.

The new tricyclic compounds according to the present invention are compounds of the general formula:

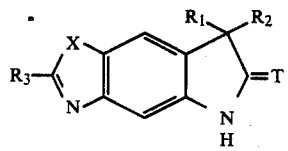 (I)

wherein $R_1$ is a hydrogen atom or an alkyl, alkenyl or cycloalkyl radical, $R_2$ is a hydrogen atom, a cyano group, an alkyl or alkenyl radical, a carbonyl group substituted by hydroxyl, alkyl, alkoxy, amino, alkylamino, dialkylamino or hydrazino or, together with $R_1$, represents a cycloalkylene radical or $R_1$ and $R_2$ together form an alkylidene or cycloalkylidene radical, T is an oxygen or sulphur atom or an $NR_4$ group, wherein $R_4$ is a hydrogen atom or an alkyl radical, $R_3$ is a hydrogen atom, a hydroxyl, amino or mercapto group, an alkylthio, pyridylcarbonylamino, alkylcarbonylamino, alkyl, cycloalkyl, alkenyl, cycloalkenyl, alkynyl, halogenoalkyl, alkoxyalkyl, carboxyalkyl or alkoxycarbonylalkyl radical and X is an oxygen or sulphur atom or an $>$N-$R_5$ group, wherein $R_5$ is a hydrogen atom or an alkyl radical, and the tautomers and physiologically acceptable salts thereof with inorganic or organic acids.

Since the compounds of general formula (I), when $R_1$ is not the same as $R_2$, contain an asymmetric carbon atom, the present invention also provides the optically-active forms and racemic mixtures of these compounds.

The new compounds according to the present invention possess valuable pharmacological properties and, in particular, they increase the power of the heart and/or have a blood pressure-lowering action and/or influence the thrombocyte aggregation and improve the microcirculation.

The above-mentioned alkyl and alkenyl moieties in the substituents $R_1$, $R_2$, $R_3$, $R_4$ and $R_5$ can be straight-chained or branched and contain 1 to 6 or 2 to 6 carbon atoms, respectively, and the cycloalkyl moieties contain 3 to 7 carbon atoms.

Preferred meanings in this sense for $R_1$ and $R_2$ include hydrogen atoms, methyl, ethyl, isopropyl, 3-pentyl, allyl, cyclopentyl, cyclohexyl, cyano, carboxyl, acetyl, propionyl, methoxycarbonyl, ethoxycarbonyl, aminocarbonyl, methylaminocarbonyl, dimethylaminocarbonyl and hydrazinocarbonyl radicals.

$R_1$ and $R_2$, together with the carbon atom to which they are attached, can also form a cycloalkyl ring containing 3 to 7 carbon atoms and preferably a spirocyclopropyl, spirocyclobutyl, spirocyclopentyl or spirocyclohexyl radical.

$R_1$ and $R_2$ can together also form a $C_3$-$C_7$ alkylidene or $C_3$-$C_7$ cycloalkylidene radical and preferably an isopropylidene or cyclohexylidene radical.

In general formula (I), $R_3$ can be a hydrogen atom, a straight-chained or branched alkyl radical containing up to 6 carbon atoms, a straight-chained or branched alkenyl or alkynyl radical containing 2 to 6 carbon atoms, a cycloalkyl or cycloalkenyl radical containing 3 to 6 carbon atoms or a halogenoalkyl radical containing up to 6 carbon atoms. Preferred substituents $R_3$ in this sense include the methyl, ethyl, propyl, butyl, pentyl, hexyl, vinyl, propenyl, butenyl pentenyl, propynyl, butynyl, cyclopropyl, cyclobutyl, cyclopentyl, cyclohexyl, cyclopentenyl, cyclohexenyl, trifluoromethyl, pentafluoroethyl and heptafluoropropyl radicals.

The substituent $R_3$ can also be hydroxyl, mercapto, amino, pyridylcarbonylamino, alkylthio, alkylcarbonylamino, alkoxyalkyl, carboxyalkyl or alkoxycarbonylalkyl. The alkyl chains can be straight-chained or branched and contain up to 6 carbon atoms. Preferred in this sense are methylthio, ethylthio, propylthio, butylthio, acetylamino, propionylamino, methoxymethyl, ethoxymethyl, methoxyethyl, ethoxyethyl, carboxymethyl, carboxyethyl, carboxypropyl, carboxybutyl, methoxycarbonylmethyl, methoxycarbonylethyl, methoxycarbonylpropyl, ethoxycarbonylmethyl, ethoxycarbonylethyl, ethoxycarbonylpropyl and propoxycarbonylethyl radicals.

T is preferably an oxygen or sulphur atom or the group $NR_4$, in which $R_4$ is a hydrogen atom or a $C_1$-$C_6$ alkyl radical.

X is preferably an oxygen atom, a sulphur atom of an $>$$NR_5$ group, in which $R_5$ is a hydrogen atom or a $C_1$-$C_6$ alkyl chain.

Especially preferred compounds of general formula (I) are those in which $R_1$ and $R_2$ are the same and represent methyl or ethyl radicals or $R_1$ and $R_2$ are different and each represents a hydrogen atom or a methyl, ethyl, isopropyl, cyclopentyl, cyano, acetyl, methoxycarbonyl, ethoxycarbonyl, aminocarbonyl or hydrazinocarbonyl radical or $R_1$ and $R_2$ represent a spirocyclopentyl ring when $R_1$ and $R_2$, together with the carbon atom to which they are attached, form a cycloalkyl ring, $R_3$ is a hydrogen atom or a methyl, ethyl, propyl, isopropyl, butyl, tert.-butyl, pentyl, hexyl, propenyl, isopropenyl, cyclopropyl, cyclopentenyl, cyclohexyl, trifluoromethyl, hydroxyl, mercapto, methylthio, amino, acetylamino, pyridylcarbonylamino, carboxyethyl, ethoxycarbonylethyl or methoxymethyl radical, X is an oxygen atom or an $>$$NR_5$ group, in which $R_5$ is a hydrogen atom or a methyl radical and T is an oxygen atom.

Further preferred compounds of general formula (I) are those wherein $R_1$ is a methyl or ethyl radical $R_2$ is a hydrogen atom or a methyl, ethyl, methoxycarbonyl or ethoxycarbonyl radical or $R_1$ and $R_2$, together with the carbon atom to which they are attached, represent a spirocyclopentyl or spirocyclohexyl radical, $R_3$ is a hydrogen atom or a methyl, ethyl, propyl, hexyl, isopropyl, propenyl, isopropenyl, tert.-butyl, cyclopropyl, cyclohexyl, cyclopentenyl, trifluoromethyl, hydroxyl, mercapto, methylthio, amino, pyridylcarbonylamino, carboxyethyl, ethoxycarbonylethyl or methoxymethyl radical, X is an oxygen atom, an imino group or an N-methylimino group and T is an oxygen atom, the tautomers thereof and the physiologically acceptable salts thereof with inorganic and organic acids.

Preparation of Compounds

The compoundsof general formula (I) and the tautomers thereof can be prepared by the processes according to the following schemes 1-6.

Scheme 1:

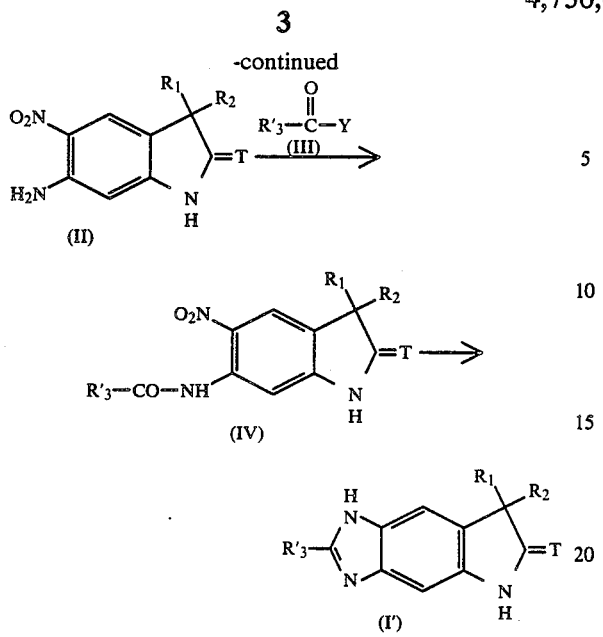

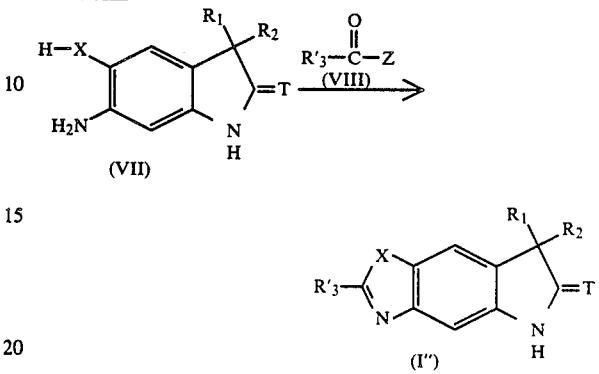

Compounds of the general formula (I') and the tautomers thereof, wherein $R_1$, $R_2$ and T have the above-given meanings and $R'_3$ is a hydrogen atom, and alkyl, cycloalkyl, alkenyl, cycloalkenyl, alkynyl, halogenoalkyl, alkoxyalkyl, carboxyalkyl or alkoxycarbonylalkyl radical, are obtained when, as shown in scheme 1, aminonitroindole derivatives of general formula (II), in which $R_1$, $R_2$ and T have the above-given meanings, are acylated with compounds of general formula (III) and the amides thereby obtained of general formula (IV) are reduced and cyclised. In the compounds of general formula (III), $R'_3$ has the above-given meaning and Y is a hydroxyl group or a residue which is easily split off. In the compounds of general formula (IV), $R_1$, $R_2$, T and $R'_3$ have the above-given meanings.

Scheme 2:

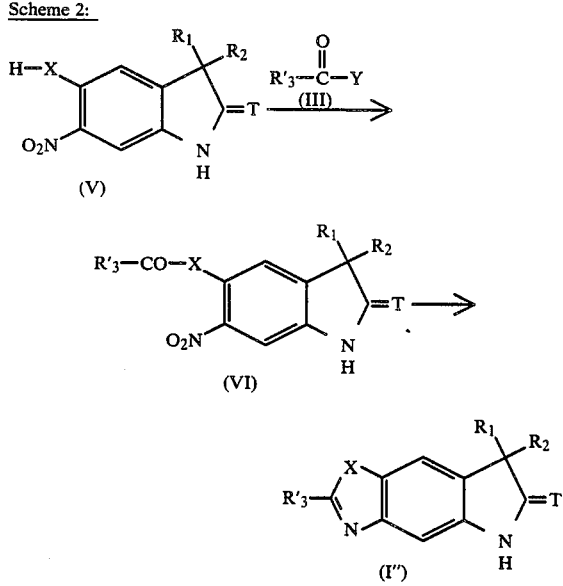

In precisely the same way, compounds of general formula (I''), in which $R_1$, $R_2$, $R'_3$, X and T have the above-given meanings, are obtained, as shown in scheme 2, when indole derivatives of general formula (V) are acylated with compounds of general formula (III) and the compounds thus obtained of general formula (VI) are subsequently reduced and cyclised. In general formulae (III), (V) and (VI), $R_1$, $R_2$, $R'_3$, X, T and Y have the above-given meanings.

Scheme 3:

As scheme 3 shows, compounds of general formula (I''), in which $R_1$, $R_2$, $R'_3$, X and T have the above-given meanings, can also be obtained when aminoindole derivatives of general formula (VII), in which $R_1$, $R_2$, T and X have the above-given meanings, are acylated with compounds of general formula (VIII) and cyclised. In general formula (VIII), $R'_3$ has the above-given meaning and Z is a hydrogen atom, a hydroxyl group or a residue which is easily split off.

By compounds of general formulae (III) and (VIII) are to be understood carboxylic acids, acid halides, such as acid chlorides, carboxylic acid esters, such as methyl and ethyl esters, and other activated carboxylic acid derivatives, for example anhydrides. In addition, compounds of general formula (VIII) can also be aldehydes.

If the compounds of general formulae (III) and (VIII) are carboxylic acids, then the acylation of compounds of general formulae (II), (V) or (VII) is carried out in the presence of a water-removing substance, such as N,N'-dicyclohexylcarbodiimide, and in a neutral solvent, such as methylene chloride, at a temperature of from $-50°$ C. to $+100°$ C. and preferably at ambient temperature or in the presence of polyphosphoric acid at a temperature of from $50°$ to $250°$ C. and preferably of from $100°$ to $200°$ C.

If the compound of general formula (III) or (VIII) is a carboxylic acid derivative, then the reaction with compounds of the general formula (II), (V) or (VII) takes place in an inert solvent, preferably in methylene chloride or pyridine.

The reduction of the nitro group in compounds of general formula (IV) or (VI) takes pace by hydrogenation in a solvent, for example water, ethanol, glacial acetic acid, ethyl acetate or dimethylformamide, preferably with hydrogen in the presence of a hydrogenation catalyst, for example Raney nickel, platinum or palladium on charcoal. The reduction can also be carried out with metals, such as iron, tin or zinc, in the presence of an acid, with salts, such as ferrous sulphate, stannous chloride, sodium sulphide, sodium hydrogen sulphide or sodium dithionite, or with hydrazine in the presence of Raney nickel. The reaction are carried out at $0°$ to $250°$ C. and preferably at ambient temperature.

The cyclisation to give compounds of general formula (I') or (I'') already takes place under the conditions of the above-mentioned reduction of the nitro group in compounds of general formula (IV) or (VI). If desired, this cyclisation can be completed by heating the reaction product from the reduction of the nitro group in a solvent or solvent mixture, such as ethanol, isopropanol, glacial acetic acid, benzene, chlorobenzene, glycol, diethylene glycol dimethyl ether, sulpholan or dimethylformamide to a temperature of from 0° to 250° C. and preferably at the boiling temperature of the solvent, optionally in the presence of a condensation agent, such as phosphorus oxychloride, thionyl chloride, p-toluenesulphonic acid, hydrochloric acid, sulphuric acid, phosphoric acid or polyphosphoric acid, or optionally also in the presence of a base, such as sodium hydroxide, potassium methylate or potassium tert.-butylate. The cyclisation can also be carried out without solvents and/or condensation agents. However, if the reaction takes place according to scheme 3, then the mentioned conditions are absolutely necessary for the cyclisation.

If the compounds of general formula (VIII) are aldehydes, then the reaction to the Schiffs base preferably takes place in an alcoholic medium and the subsequent cyclisation and oxidation takes place by heating the reaction mixture to reflux in the presence of atmospheric oxygen and catalytic amounts of an acid, for example acetic acid or toluenesulphonic acid, and optionally of catalytic amounts of manganese dioxide.

Scheme 4:

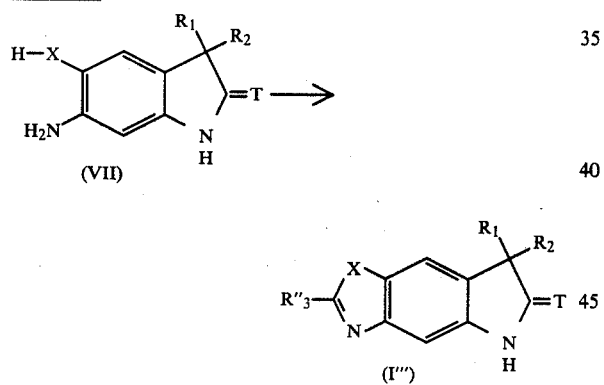

As can be seen from scheme 4, compounds of general formula (VII) can also be cyclised to give compounds of general formula (I'''), in which $R_1$, $R_2$, T and X have the above-given meanings and $R_3''$ is a hydroxyl, mercapto or amino group. This takes place by reaction with reagents which transfer carbonyl groups or the equivalents thereof, such as thiocarbonyl or imino groups, preferably with phosgene, 1,1'-carbonyldiimidazole, thiophosgene or cyanogen bromide.

These reactions are carried out in a solvent or solvent mixture, such as benzene, toluene, chlorobenzene, dimethylformamide or aqueous hydrochloric acid, at a temperature of from −20° to +100° C. and preferably at ambient temperature.

Scheme 5:

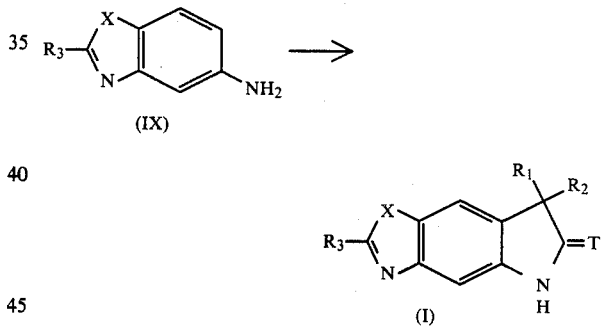

Compounds of general formula (I''''), in which $R_1$, $R_2$, T and X have the same meanings as above, can be prepared by reacting compounds of general formula (II) or (V) with haloformic acid esters, preferably with ethyl chloroformate, subsequently reducing the nitro group and cyclising. This reduction and cyclisation takes place under the conditions described hereinbefore.

Scheme 6:

$$R_3-\overset{X}{\underset{N}{\diagup}}-NH_2 \longrightarrow$$

(IX)

$$R_3-\overset{X}{\underset{N}{\diagup}}-\overset{R_1\ R_2}{\underset{\underset{H}{N}}{\diagdown}}=T$$

(I)

Compounds of general formula (IX) can, as shown in scheme 6, be cyclised by processes known from the literature to give compounds of the general formula (I), in which $R_1$, $R_2$, $R_3$, T and X have the above-given meanings. This takes place with bisulphite addition compounds of appropriate ketones (Hinsberg synthesis) or via appropriate hydrazide (Brunner synthesis) or via appropriate amides (Stolle synthesis). In this regard, see R. C. Elderfield (editor), P. L. Julian, E. W. Meyer and H. C. Printy in "Heterocyclic Compounds", Volume 3, pp. 126–186, pub. J. Wiley and Sons, New York, 1952.

A compound obtained according to the present invention of general formula (I) or a tautomer thereof can, if desired, also be converted into another compound of general formula (I). This applies, for example, to:

(a) The conversion of compounds of general formula (I), in which $R_1$ and $R_2$ are hydrogen atoms, to give compounds of general formula (I), in which $R_1$ together with $R_2$ represents an isopropylidene, cyclopentylidene or cyclohexylidene radical, as well as possibly the hydrogenation thereof to give compounds of general formula (I), wherein $R_1$ or $R_2$ are hydrogen atoms.

This concerns, for example, the reaction with compounds of the general formula:

$$R_6-CO-R_7 \qquad (X),$$

wherein $R_6$ and $R_7$ are alkyl radicals or $R_6$ and $R_7$ together form a $C_3-C_7$ cycloalkylene radical, in the presence of a base, for example ammonia or triethylamine, in alcoholic solution.

(b) The subsequent conversion of compounds of general formula (I), in which $R_1$ or $R_2$ is a carboxyl group or a reactive derivative, for example a carboxylic acid ester or acid chloride, with hydrazine, ammonia, a primary or secondary amine or a reactive derivative thereof, to give new compounds of general formula (I), in which $R_1$ or $R_2$ is a carbonyl group substituted by an amino, alkylamino, dialkylamino or hydrazino group. The subsequent conversion also applied to compounds of general formula (I), in which $R_1$ or $R_2$ is an aminocarbonyl group to those in which $R_1$ or $R_2$ is a cyano group, as well as the subsequent conversion of a cyano group into a carboxyl, aminocarbonyl or alkylcarbonyl group.

The reaction of carboxylic acid derivatives with amine derivatives is preferably carried out in a solvent or solvent mixture, such as methylene chloride, ethanol, chloroform, carbon tetrachloride, diethyl ether, tetrahydrofuran, dioxan, benzene, toluene, acetonitrile or dimethylformamide, optionally in the presence of an agent activating the acid or of a water-removing agent, for example in the presence of ethyl chloroformate, thionyl chloride, phosphorus trichloride, phosphorus pentoxide, N,N'-dicyclohexylcarbodiimide/N-hydroxysuccinimide, N,N'-carbonyldiimidazole or N,N'-thionyldiimidazole or triphenylphosphine/carbon tetrachloride, or of a hydrazino- or amino group-activating agent, for example phosphorus trichloride, and optionally in the presence of an inorganic base, such as sodium carbonate, or of a tertiary organic base, such as triethylamine or pyridine, which can simultaneously serve as solvent, at a temperature of from $-25°$ to $+250°$ C. but preferably at a temperature of from $-10°$ C. to the boiling temperature of the solvent used. Furthermore, water formed during the reaction can be separated off by azeotropic distillation, for example by heating with toluene on a water separator or by the addition of a drying agent, for example anhydrous magnesium sulphate or of a molecular sieve.

However, the reaction is carried out especially advantageously in an appropriate halide, for example the carboxylic acid or sulphonic acid chloride, and hydrazine or a corresponding amine, whereby these can simultaneously serve as solvents, and at a temperature of from $0°$ to $50°$ C.

The reaction to give a cyano group is preferably carried out in an inert solvent, for example in methylene chloride, chloroform, dioxan, pyridine, xylene or chlorobenzene, in the presence of a water-removing agent, for example thionyl chloride, phosphorus trichloride, phosphorus pentoxide, phosphorus pentachloride, aluminium chloride, benzenesulphonic acid chloride, toluenesulphonic acid chloride, triphenylphosphine, boron trifluoride or a polyphosphoric acid ester, at a temperature of from $50°$ to $250°$ C. but preferably at the boiling temperature of the solvent.

If a compound is obtained of general formula (I) in which $R_2$ is a cyano group, then this can subsequently be converted by alcoholysis and/or hydrolysis into a corresponding compound in which $R_2$ is an alkoxycarbonyl radical with a total of 2 to 5 carbon atoms, an aminocarbonyl or carboxyl group and/or a compound of general formula (I) in which $R_2$ is a carboxyl group can be converted by esterification into a corresponding compound of general formula (I) in which $R_2$ is an alkoxycarbonyl radical with a total of 2 to 5 carbon atoms.

The subsequent alcoholysis and/or hydrolysis is preferably carried out either in the presence of an acid, such as hydrochloric acid, sulphuric acid, phosphoric acid or trichloroacetic acid, or in the presence of a base, such as sodium hydroxide or potassium hydroxide, in an appropriate solvent, such as water, water/methanol, ethanol, water/ethanol, water/isopropanol or water/dioxan, at a temperature of from $-10°$ to $+120°$ C., for example at a temperature of from ambient temperature to the boiling temperature of the reaction mixture.

The subsequent esterification is preferably carried out in an appropriate solvent, for example in a corresponding alcohol, pyridine, toluene, methylene chloride, tetrahydrofuran or dioxan, in the presence of an acid-activating and/or water-removing agent, such as thionyl chloride, ethyl chloroformate, N,N'-carbonyldiimidazole or N,N'-dicyclohexylcarbodiimide or an isourea ether thereof, optionally in the presence of a reaction accelerator, such as copper chloride, or by transesterification, for example with an appropriate carbonic acid ester, at a temperature of from $0°$ to $100°$ C. but preferably at a temperature of from $20°$ C. to the boiling temperature of the solvent in question.

(c) These esterification conditions can also be used in order to convert compounds of general formula (I), in which $R_1$, $R_2$, T and X have the above-given meanings and $R_3$ is a carboxyalkyl radical, into other compounds of general formula (I), in which $R_3$ is an alkoxycarbonylalkyl radical.

(d) Compounds of general formula (I), in which $R_1$, $R_3$, T and X have the above-given meanings and $R_2$ is an alkoxycarbonyl radical, can be converted into compounds of general formula (I), in which $R_2$ is a hydrogen atom. This takes place by saponification of the alkoxycarbonyl radical and decarboxylation. The saponification is preferably carried out in the presence of an acid, such as hydrochloric acid, sulphuric acid, phosphoric acid or trichloroacetic acid, or in the presence of a base, such as sodium hydroxide or potassium hydroxide, in an appropriate solvent, such as water or water/dioxan, at a temperature of from $0°$ to $120°$ C. and preferably at the boiling temperature of the reaction mixture. The decarboxylation thereby usually takes place spontaneously. If desired, it can be accelerated by increasing the reaction temperature.

(e) The subsequent conversion into compounds of general formula (I) and the intermediate products leading to compounds of general formula (I) in which T is a sulphur atom from those in which T is an oxygen atom is carried out by processes known from the literature with a reagent transferring the sulphur atom, for example phosphorus pentasulphide or 2,4-bis-(4-methoxyphenyl)-2,4-dithioxo-1,3,2,4-dithiaphosphetane, in an appropriate solvent, for example tetrahydrofuran, dioxan, ethylene glycol dimethyl ether, benzene, toluene or pyridine, at a temperature of from $0°$ C. to the boiling temperature of the reaction mixture.

(f) The subsequent alkylation of compounds of general formula (I) in which $R_3$ is a mercapto group to give compounds of general formula (I) in which $R_3$ is an alkylthio radical are preferably carried out in a solvent, such as acetone, diethyl ether, benzene, toluene or dimethylformamide, at a temperature of from −30° to +100° C. and preferably at ambient temperature in the presence of a base, such as potassium carbonate or sodium hydride, and of an alkylation agent, such as an alkyl halide or alkyl sulphate.

(g) The subsequent acylation of compounds of general formula (I), in which $R_3$ is an amino group, into compounds of general formula (I) in which $R_3$ is an acylamino radical are preferably carried out by reaction with carboxylic acid derivatives, such as acid halides, carboxylic acid esters or other activated carboxylic acid derivatives, such as anhydrides.

(h) Compounds of general formula (I), in which $R_1$, $R_2$, $R_3$ and X have the above-given meanings and T is an oxygen atom, can be converted into compounds of general formula (I), in which T is an $NR_4$ group. This preferably takes place by converting compounds of general formula (I), in which T is an oxygen atom, in the presence of phosphorous pentachloride or phosphorus oxychloride, into the imide chloride and this is allowed to react with ammonia or a primary amine at a temperature of from 0° to 100° C. or by reacting a compound of general formula (I), in which T is a sulphur atom, with ammonia or a primary alkylamine at a temperature of from 80° to 200° C.

The compounds of general formula (I), in which $R_1$, $R_2$, $R_3$ and T have the above-given meanings, and the tautomers thereof can, if desired, be converted into their pharmacologically acceptable salts. For this purpose, they are preferably reacted in an organic solvent with an equivalent amount of an inorganic or organic acid, for example hydrochloric acid, hydrobromic acid, phosphoric acid, sulphuric acid, acetic acid, citric acid, tartaric acid, maleic acid, fumaric acid, benzoic acid or cyclohexylsulphaminic acid.

For the preparation of pharmaceutical compositions, the compounds of general formula (I) are mixed in known manner with appropriate pharmaceutical carrier substances, aroma, flavouring and colouring materials and formed, for example, into tablets or dragees or, with the addition of appropriate adjuvants, are suspended or dissolved in water or an oil, for example olive oil.

The new compounds according to the present invention of general formula (I) and the salts thereof can be administered enterally or parenterally in liquid or solid form. As injection medium, it is preferable to use water which contains the additives usual in the case of injection solutions, such as stabilising agents, solubilising agents or buffers.

Additives of this kind include, for example, citrate and tartrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds according to the present invention are usually administered in amounts of from 0.1 to 500 mg. per day, referred to a body weight of 75 kg. It is preferred to administer 2 or 3 times a day 1 to 2 tablets with an active material content of 0.1 to 200 mg. The tablets can also be retarded, whereby per day only 1 to 2 tablets with 0.1 to 500 mg. of active material have to be given. The active material can also be administered by injection 1 to 8 times per day or by continuous infusion, in which case amounts of from 0.1 to 200 mg. per day normally suffice.

Preferred compounds according to the present invention, apart from those described in the following Examples, are the following compounds and the tautomers thereof:

2-methyl-6,7-dihydro-3H,5H-pyrrolo[2,3-f]benzimidazol-6-one 7-acetyl-2-methyl-6,7-dihydro-3H,5H-pyrrolo[2,3-f]benzimidazol-6-one 7-acetyl-2,7-dimethyl-6,7-dihydro-3H,5H-pyrrolo[2,3-f]benzimidazol-6-one 7-allyl-2-methyl-6,7-dihydro-3H,5H-pyrrolo[2,3-f]benzimidazol-6-one 7-aminocarbonyl-2,7-dimethyl-6,7-dihydro-3H,5H-pyrrolo[2,3-f]benzimidazol-6-one 7-cyano-2,7-dimethyl-6,7-dihydro-3H,5H-pyrrolo[2,3-f]benzimidazol-6-one 7-cyclohexyl-2-methyl-6,7-dihydro-3H,5H-pyrrolo[2,3-f]benzimidazol-6-one 7,7-diallyl-2-methyl-6,7-dihydro-3H,5H-pyrrolo[2,3-f]benzimidazol-6-one 7,7-diethyl-2-methyl-6,7-dihydro-3H,5H-pyrrolo[2,3-f]benzimidazol-6-one 7-ethoxycarbonyl-2-methyl-6,7-dihydro-3H,5H-pyrrolo[2,3-f]benzimidazol-6-one 7-ethoxycarbonyl-2,7-dimethyl-6,7-dihydro-3H,5H-pyrrolo[2,3-f]benzimidazol-6-one 7-hydrazinocarbonyl-2,7-dimethyl-6,7-dihydro-3H,5H-pyrrolo[2,3-f]benzimidazol-6-one 7-isopropylidene-2-methyl-6,7-dihydro-3H,5H-pyrrolo[2,3-f]benzimidazol-6-one 7-methoxycarbonyl-2-methyl-6,7-dihydro-3H,5H-pyrrolo[2,3-f]benzimidazol-6-one 7-methoxycarbonyl-2,7-dimethyl-6,7-dihydro-3H,5H-pyrrolo[2,3-f]benzimidazol-6-one 2,7-dimethyl-6,7-dihydro-3H,5H-pyrrolo[2,3-f]benzimidazol-6-one 7-(2-methylpropyl)-2-methyl-6,7-dihydro-3H,5H-pyrrolo[2,3-f]benzimidazol-6-one 7-(3-pentyl)-2-methyl-6,7-dihydro-3H,5H-pyrrolo[2,3-f]benzimidazol-6-one 7-(2-propyl)-2-methyl-6,7-dihydro-3H,5H-pyrrolo[2,3-f]benzimidazol-6-one 2'-methylspiro[cyclopentan-1,7'-6',7'-dihydro-3'H,5'H-pyrrolo[2',3'-f]benzimidazol-6'-one 7-acetyl-7-methyl-2-hydroxy-6,7-dihydro-3H,5H-pyrrolo[2,3-f]benzimidazol-6-one 7-propyl-2-hydroxy-6,7-dihydro-3H,5H-pyrrolo[2,3-f]benzimidazol-6-one 7-aminocarbonyl-2-hydroxy-6,7-dihydro-3H,5H-pyrrolo[2,3-f]benzimidazol-6-one 7-cyano-2-hydroxy-6,7-dihydro-3H,5H-pyrrolo[2,3-f]benzimidazol-6-one 7-ethoxycarbonyl-2-hydroxy-6,7-dihydro-3H,5H-pyrrolo[2,3-f]benzimidazol-6-one 7-hydrazinocarbonyl-2-hydroxy-6,7-dihydro-3H,5H-pyrrolo[2,3-f]benzimidazol-6-one 7-isopropylidene-2-hydroxy-6,7-dihydro-3H,5H-pyrrolo[2,3-f]benzimidazol-6-one
7-methoxycarbonyl-7-methyl-2-hydroxy-6,7-dihydro-3H,5H-pyrrolo[2,3-f]benzimidazol-6-one
7-(2-propyl)-2-hydroxy-6,7-dihydro-3H,5H-pyrrolo[2,3-f]benzimidazol-6-one
2'-hydroxyspiro[cyclopentan-1,7'-6',7'-dihydro-3'H,5'H-pyrrolo[2',3'-f]benzimidazol]-6'-one
7-acetyl-7-methyl-6,7-dihydro-3H,5H-pyrrolo[2,3-f]benzimidazol-6-one
7-ethoxycarbonyl-7-methyl-6,7-dihydro-3H,5H-pyrrolo[2,3-f]benzimidazol-6-one
7-acetyl-7-methyl-2-propyl-6,7-dihydro-3H,5H-pyrrolo[2,3-f]benzimidazol-6-one
7-ethyl-2-propyl-6,7-dihydro-3H,5H-pyrrolo[2,3-f]benzimidazol-6-one
7-ethoxycarbonyl-7-methyl-2-propyl-6,7-dihydro-3H,5H-pyrrolo[2,3-f]benzimidazol-6-one
7-acetyl-7-methyl-2-(2-propyl)-6,7-dihydro-3H,5H-pyrrolo[2,3-f]benzimidazol-6-one
7-methyl-2-(2-propyl)-6,7-dihydro-3H,5H-pyrrolo[2,3-f]benzimidazol-6-one
7-ethyl-2-(2-propyl)-6,7-dihydro-3H,5H-pyrrolo[2,3-f]benzimidazol-6-one
7-ethoxycarbonyl-7-methyl-2-(2-propyl)-6,7-dihydro-3H,5H-pyrrolo[2,3-f]benzimidazol-6-one
2'-(2-propyl)-spiro[cyclopentan-1,7'-6',7'-dihydro-3'H,5'H-pyrrolo[2',3'-f]benzimidazol]-6'-one
7-acetyl-7-methyl-2-cyclohexyl-6,7-dihydro-3H,5H-pyrrolo[2,3-f]benzimidazol-6-one
7-methyl-2-cyclohexyl-6,7-dihydro-3H,5H-pyrrolo[2,3-f]benzimidazol-6-one
7-ethyl-2-cyclohexyl-6,7-dihydro-3H,5H-pyrrolo[2,3-f]benzimidazol-6-one
7-ethoxycarbonyl-7-methyl-2-cyclohexyl-6,7-dihydro-3H,5H-pyrrolo[2,3-f]benzimidazol-6-one
2'-cyclohexyl-spiro[cyclopentan-1,7'-6',7'-dihydro-3'H,5'H-pyrrolo[2',3'-f]benzimidazol]-6'one
7-acetyl-7-methyl-2-(2-propenyl)-6,7-dihydro-3H,5H-pyrrolo[2,3-f]benzimidazol-6-one
7-methyl-2-(2-propenyl)-6,7-dihydro-3H,5H-pyrrolo[2,3-f]-benzimidazol-6-one
7-ethyl-2-(2-propenyl)-6,7-dihydro-3H,5H-pyrrolo[2,3-f]benzimidazol-6-one
7-ethoxycarbonyl-7-methyl-2-(2-propenyl)-6,7-dihydro-3H,5H-pyrrolo[2,3-f]benzimidazol-6-one
2'-(2-propenyl)-spiro[cyclopentan-1,7'-6',7'-dihydro-3'H,5'H-pyrrolo[2',3'-f]benzimidazol]-6'-one
7-acetyl-7-methyl-2-(1-cyclopentenyl)-6,7-dihydro-3H,5H-pyrrolo[2,3-f]benzimidazol-6-one
7-methyl-2-(1-cyclopentenyl)-6,7-dihydro-3H,5H-pyrrolo[2,3-f]benzimidazol-6-one
7-ethyl-2-(1-cyclopentenyl)-6,7-dihydro-3H,5H-pyrrolo-[2,3-f]benzimidazol-6-one
7-ethoxycarbonyl-7-methyl-2-(1-cyclopentenyl)-6,7-dihydro-3H,5H-pyrrolo[2,3-f]benzimidazol-6-one
2'-(1-cyclopentenyl)-spiro[cyclopentan-1,7'-6',7'-dihydro-3'H,5'H-pyrrolo[2',3'-f]benzimidazol]-6'-one
7-acetyl-7-methyl-2-trifluoromethyl-6,7-dihydro-3H,5H-pyrrolo[2,3-f]benzimidazol-6-one
7-methyl-2-trifluoromethyl-6,7-dihydro-3H,5H-pyrrolo[2,3-f]benzimidazol-6-one
7-ethyl-2-trifluoromethyl-6,7-dihydro-3H,5H-pyrrolo[2,3-f]benzimidazol-6-one
7-ethoxycarbonyl-7-methyl-2-trifluoromethyl-6,7-dihydro-3H,5H-pyrrolo[2,3-f]benzimidazol-6-one
2'-trifluoromethyl-spiro[cyclopentan-1,7'-6',7'-dihydro-3'H,5'H-pyrrolo[2',3'-f]benzimidazol]-6'-one
7-acetyl-7-methyl-2-mercapto-6,7-dihydro-3H,5H-pyrrolo[2,3-f]benzimidazol-6-one
7-methyl-2-mercapto-6,7-dihydro-3H,5H-pyrrolo[2,3-f]benzimidazol-6-one
7-ethyl-2-mercapto-6,7-dihydro-3H,5H-pyrrolo[2,3-f]benzimidazol-6-one
7-ethoxycarbonyl-7-methyl-2-mercapto-6,7-dihydro-3H,5H-pyrrolo[2,3-f]benzimidazol-6-one
2'-mercaptospiro[cyclopentan-1,7'-6',7'-dihydro-3'H,5'H-pyrrolo[2',3'-f]benzimidazol]-6'-one
7-acetyl-7-methyl-2-amino-6,7-dihydro-3H,5H-pyrrolo[2,3-f]benzimidazol-6-one
7-methyl-2-amino-6,7-dihydro-3H,5H-pyrrolo[2,3-f]benzimidazol-6-one
7-ethyl-2-amino-6,7-dihydro-3H,5H-pyrrolo[2,3-f]benzimidazol-6-one
7-ethoxycarbonyl-7-methyl-2-amino-6,7-dihydro-3H,5H-pyrrolo[2,3-f]benzimidazol-6-one
2'-amino-spiro[cyclopentan-1,7'-6',7'-dihydro-3'H,5'H-pyrrolo[2',3'-f]benzimidazol]-6'-one
7-acetyl-7-methyl-acetamino-6,7-dihydro-3H,5H-pyrrolo[2,3-f]benzimidazol-6-one
7-methyl-2-acetamino-6,7-dihydro-3H,5H-pyrrolo[2,3-f]benzimidazol-6-one
7-ethyl-2-acetamino-6,7-dihydro-3H,5H-pyrrolo[2,3-f]benzimidazol-6-one
7-ethoxycarbonyl-7-methyl-2-acetamino-6,7-dihydro-3H,5H-pyrrolo[2,3-f]benzimidazol-6-one
2'-acetamino-spiro[cyclopentan-1,7'-6',7'-dihydro-3'H,5'H-pyrrolo[2',3'-f]benzimidazol]-6'-one
7,7-dimethyl-2-acetamino-6,7-dihydro-3H,5H-pyrrolo[2,3-f]benzimidazol-6-one
7-acetyl-7-methyl-2-methylthio-6,7-dihydro-3H,5H-pyrrolo[2,3-f]benzimidazol-6-one
7-methyl-2-methylthio-6,7-dihydro-3H,5H-pyrrolo[2,3-f]benzimidazol-6-one
7-ethyl-2-methylthio-6,7-dihydro-3H,5H-pyrrolo[2,3-f]benzimidazol-6-one
7-ethoxycarbonyl-7-methyl-2-methylthio-6,7-dihydro-3H,5H-pyrrolo[2,3-f]benzimidazol-6-one
2'-methylthiospiro[cyclopentan-1,7'-6',7'-dihydro-3'H,5'H-pyrrolo[2',3'-f]benzimidazol]-6'one
7,7-dimethyl-2-ethyl-6,7-dihydro-3H,5H-pyrrolo[2,3-f]benzimidazol-6-one
7,7-dimethyl-2-(1-butyl)-6,7-dihydro-3H,5H-pyrrolo[2,3-f]benzimidazol-6-one
7,7-dimethyl-2-(2-butyl)-6,7-dihydro-3H,5H-pyrrolo[2,3-f]benzimidazol-6-one
7,7-dimethyl-2-ethenyl-6,7-dihydro-3H,5H-pyrrolo[2,3-f]benzimidazol-6-one
7,7-dimethyl-2-(1,2-dimethylethenyl)-6,7-dihydro-3H,5H-pyrrolo[2,3-f]benzimidazol-6-one
7,7-dimethyl-2-(2,2-dimethylethenyl)-6,7-dihydro-3H,5H-pyrrolo[2,3-f]benzimidazol-6-one
7,7-dimethyl-2-(1-butenyl)-6,7-dihydro-3H,5H-pyrrolo[2,3-f]benzimidazol-6-one
7,7-dimethyl-2-(4-butenyl)-6,7-dihydro-3H,5H-pyrrolo[2,3-f]benzimidazol-6-one
7,7-dimethyl-2-(1-hexenyl)-6,7-dihydro-3H,5H-pyrrolo[2,3-f]benzimidazol-6-one
7,7-dimethyl-2-(2-hexenyl)-6,7-dihydro-3H,5H-pyrrolo[2,3-f]benzimidazol-6-one
7,7-dimethyl-2-(1-methyl-1-butenyl)-6,7-dihydro-3H,5H-pyrrolo[2,3-f]benzimidazol-6-one
7,7-dimethyl-2-(1-methylcyclopropyl)-6,7-dihydro-3H,5H-pyrrolo[2,3-f]benzimidazol-6-one
7,7-dimethyl-2-(2-methylcyclopropyl)-6,7-dihydro-3H,5H-pyrrolo[2,3-f]benzimidazol-6-one 7,7-dimethyl-2-cyclobutyl-6,7-dihydro-3H,5H-pyrrolo[2,3-f]benzimidazol-6-one
7,7-dimethyl-2-cyclopentyl-6,7-dihydro-3H,5H-pyrrolo[2,3-f]benzimidazol-6-one
7,7-dimethyl-2-cyclohexenyl-6,7-dihydro-3H,5H-pyrrolo[2,3-f]benzimidazol-6-one
7,7-dimethyl-2-pentafluoroethyl-6,7-dihydro-3H,5H-pyrrolo[2,3-f]benzimidazol-6-one
7,7-dimethyl-2-heptafluoropropyl-6,7-dihydro-3H,5H-pyrrolo[2,3-f]benzimidazol-6-one
7,7-dimethyl-2-ethylthio-6,7-dihydro-3H,5H-pyrrolo[2,3-f]-benzimidazol-6-one
7,7-dimethyl-2-propylthio-6,7-dihydro-3H,5H-pyrrolo[2,3-f]benzimidazol-6-one
7,7-dimethyl-2-ethylcarbonylamino-6,7-dihydro-3H,5H-pyrrolo[2,3-f]benzimidazol-6-one
7,7-dimethyl-2-propylcarbonylamino-6,7-dihydro-3H,5H-pyrrolo[2,3-f]benzimidazol-6-one
7,7-dimethyl-2-(3-pyridylcarbonylamino)-6,7-dihydro-3H,5H-pyrrolo[2,3-f]benzimidazol-6-one
7,7-dimethyl-2-cyclopentenyl-6,7-dihydro-3H,5H-pyrrolo[2,3-f]benzimidazol-6-one
2,7,7-trimethyl-6,7-dihydro-3H,5H-pyrrolo[2,3-f]benzimidazol-6-thione
2,7-dimethyl-6,7-dihydro-3H,5H-pyrrolo[2,3-f]benzimidazol-6-thione
1-ethyl-2-hydroxy-7,7-dimethyl-6,7-dihydro-3H,5H-pyrrolo[2,3-f]benzimidazol-6-one
1-propyl-2-hydroxy-7,7-dimethyl-6,7-dihydro-5H-pyrrolo[2,3-f]benzimidazol-6-one
1-methyl-2-hydroxy-6,7-dihydro-5H-pyrrolo[2,3-f]benzimidazol-6-one
1-methyl-2-hydroxy-7-ethoxycarbonyl-7-methyl-6,7-dihydro-5H-pyrrolo[2,3-f]benzimidazol-6-one
2,7,7-trimethyl-6-methylimino-6,7-dihydro-3H,5H-pyrrolo[2,3-f]benzimidazole
2,7,7-trimethyl-6,7-dihydro-5H-pyrrolo[2,3-f]benzthiazol-6-one
7,7-dimethyl-2-hydroxy-6,7-dihydro-5H-pyrrolo[2,3-f]benzthiazol-6-one The following Examples are given for the purpose of illustrating the present invention:

EXAMPLE 1

7,7-Dimethyl-6,7-dihydro-3H,5H-pyrrolo[2,3-f]-benzimidazol-6-one 288 mg. (1.51 mmole) 5,6-diamino-3,3-dimethylindolin-2-one and 66 mg. (1.43 mmole) formic acid are heated for 1 hour at 100° C. After the addition of a further 24 mg. (0.52 mmole) formic acid, the reaction mixture is further heated to 100° C. for 60 minutes. Thereafter, trituration is carried out with 0.5 ml. amounts of diethyl ether, followed by suction filtration. There are obtained 277 mg. (91% of theory) of the title compound in the form of pale crystals; m.p. 278°–280° C.

EXAMPLE 2

7,7-Dimethyl-2-cyclohexyl-6,7-dihydro-3H,5H-pyrrolo[2,3-f]benzimidazol-6-one

Analogously to Example 1, from 960 mg. (5.0 mmole) 5,6-diamino-3,3-dimethylindolin-2-one and 640 mg. (5.0 mmole) cyclohexanecarboxylic acid, after 1.5 hours at 240° C., there is obtained 1.37 g. of crude product. 300 mg. thereof are purified over a silica gel column (elution agent: dichloromethane/methanol 9:1 v/v). After removal of the solvent in a vacuum, there is obtained a greenish oil which is crystallised with diethyl ether.

There are obtained 192 mg. (53% of theory) of the title compound in the form of pale brown crystals; m.p. 315°–318° C.

EXAMPLE 3

2'-Propylspiro[cyclopentane-1,7'-6',7'-dihydro-3'H,5'H-pyrrolo[2',3'-f]benzimidazol]-6'-one Analogously to Example 1, a solution of 6.0 g. (27.6 mmole) 5',6'-diaminospiro[cyclopentone-1,3'-2',3'-dihydroindol]-2'-one, 5.4 ml. (33.0 mmole) butyric acid anhydride and 60 ml. concentrated hydrochloric acid is heated under reflux for 15 hours in 250 ml. methanol. The solution is evaporated to dryness in a vacuum and the residue is separated over a silica gel column (length 70 cm., diameter 6 cm., elution agent: dichloromethane:methanolic ammonia solution 9:1 v/v). The appropriate fractions are evaporated to dryness in a vacuum and the residue is recrystallised from methanol, with the addition of active charcoal. There are obtained 3.0 g. (41% of theory) of the title compound; m.p. 332°–335° C.

EXAMPLE 4

2-(2-Carboxyethyl)-7,7-dimethyl-6,7-dihydro-3H,5H-pyrrolo[2,3-f]benzimidazol-6-one Analogously to Example 1, a solution of 3.82 g. 5,6-diamino-3,3-dimethylindolin-2-one and 2.36 g. succinic acid in 10 ml. 4N hydrochloric acid is heated for 4 hours at 135° C. (bath temperature). The reaction mixture is then evaporated in a vacuum until a thick slurry has formed. 10 ml. water are added thereto and the pH is adjusted to 10 with concentrated aqueous ammonia solution. Insoluble material is filtered off with suction and washed with water and the filtrate is treated with charcoal, filtered and the filtrate evaporated in a vacuum. The evaporation residue is taken up in 10 ml. water and acidified with glacial acetic acid, the title compound thereby precipitating out. After drying for 4 hours in a vacuum at 60° C., there are obtained 2.2 g. of desired compound with a melting point of 130°–135° C. (foaming). This compound contains 1.6 mole of water per mole of compound.

An 80 mg. sample thereof is dissolved in isopropanol, treated with active charcoal and filtered. The clear filtrate is concentrated to about 0.5 ml., there thus being obtained 30 mg. of the title compound which still contains 0.5 mole of water; m.p. 216°–218° C.

EXAMPLE 5

7,7-Dimethyl-2-(2-propyl)-6,7-dihydro-3H,5H-pyrrolo[2,3-f]benzimidazol-6-one (a) 1.65 g. (7.5 mmole) 6-Amino-5-nitro-3,3-dimethylindolin-2-one and 2.42 g. isobutyric acid anhydride in 15 ml. pyridine are maintained at 50° C. for 1 hour. After 1 hour, 1.2 g. isobutyric acid anhydride is added thereto and the reaction mixture is kept at 50° C. for 1 hour. The solvent is removed in a high vacuum and the residue is dissolved in 30 ml. dichloromethane. 30 ml. ice water are added thereto, followed by neutralisation with sodium hydrogen carbonate (pH 7–8). The mixture is extracted four times with dichloromethane and the combined dichloromethane phases are combined and treated with active charcoal. After filtration and removal of the solvent, the residue is triturated with diethyl ether. There is obtained 1.1 g. (50% of theory)

6-isobutyric acid amido-5-nitro-3,3-dimethylindolin-2-one; m.p. 138°–140° C.

(b) The above residue is hydrogenated in 200 ml. methanol in the presence of 400 mg. 10% palladium on active charcoal for 1 hour. After filtration and removal of the solvent in a vacuum, there is obtained 0.8 g. 5-amino-6-isobutyric acid amido-3,3-dimethylindolin-2-one as an amorphous substance which is used without further purification.

(c) The residue from (b) is suspended in 8 ml. isobutyric acid and stirred for 1 hour at 100° C. The reaction mixture is evaporated in a high vacuum, the residue is mixed with 50 ml. ice water and the pH is adjusted to 8 with an aqueous solution of ammonia. It is then extracted with ethyl acetate, dried and treated with active charcoal. After filtering, the filtrate is concentrated to about 10 ml. and, after 30 minutes, the precipitated crystals are filtered off with suction. There is obtained 0.37 g. (40% of theory) of the title compound; m.p. 282°–284° C.

EXAMPLE 6

2-(1-Propyl)-7,7-dimethyl-6,7-dihydro-3H,5H-pyrrolo[2,3-f]benzimidazol-6-one

According to the process of Example 5, from 0.7 g. (2.7 mmole) 5-amino-6-n-propylcarbonylamino-3,3-dimethylindolin-2-one and 7 ml. butyric acid, after 1 hour at 100° C., there is obtained 0.4 g. (61% of theory) of the title compound; m.p. 284°–285° C.

EXAMPLE 7

7,7-Dimethyl-2-trifluoromethyl-6,7-dihydro-3H,5H-pyrrolo[2,3-f]benzimidazol-6-one Analogously to Example 5, 4.50 g. (0.014 mole) 6-trifluoroacetamido-5-nitro-3,3-dimethylindolin-2-one in 500 ml. ethanol are hydrogenated in the presence of 0.5 g. 10% palladium on charcoal at normal pressure and at ambient temperature. After filtration, the filtrate is evaporated to dryness in a vacuum and the residue is dissolved in dichloromethane/ethyl acetate and treated with active charcoal. After filtration, the filtrate is evaporated to dryness in a vacuum and the residue is recrystallised from ethyl acetate, there being obtained 3.8 g. (95% of theory) of the title compound in the form of the monohydrate; m.p. 175°–177° C.

EXAMPLE 8

2,7,7-Trimethyl-6,7-dihydro-3H,5H-pyrrolo[2,3-f]benzimidazol-6-one

Analogously to Example 5, 5.00 g. (0.019 mole) 6-acetamido-5-nitro-3,3-dimethylindolin-2-one are suspended in 900 ml. glacial acetic acid and hydrogenated in the presence of 0.5 g. platinum dioxide at normal pressure and ambient temperature. After 1.4 liters of hydrogen have been taken up, the reaction mixture is filtered and the filtrate is evaporated to dryness in a vacuum. The residue is taken up in water and neutralised with a 2N aqueous ammonia solution. The precipitate obtained is filtered off with suction and recrystallised from ethyl acetate. There are obtained 2.75 g. (67% of theory) of the title compound; m.p. >300° C.

EXAMPLE 9

2-Methoxymethyl-7,7-dimethyl-6,7-dihydro-3H,5H-pyrrolo[2,3-f]benzimidazol-6-one

Analogously to Example 5, 1.6 g. (5.4 mmole) 6-methoxymethylcarbonylamino-5-nitro-3,3-dimethylindolin-2-one are dissolved in 160 ml. ethanol and hydrogenated in the presence of 0.8 g. 10% palladium on charcoal at normal pressure and ambient temperature. After 360 ml. of hydrogen have been taken up, the catalyst is filtered off with suction and the filtrate is evaporated to dryness in a vacuum. The residue is purified over a silica gel column (elution agent: dichloromethane/methanol 95:5 v/v). The appropriate fractions are evaporated to dryness and the residue is recrystallised from isopropanol. There are obtained 800 mg. (60% of theory) of the title compound; m.p. 203°–205° C.

EXAMPLE 10

2-Propyl-7-ethoxycarbonyl-7-methyl-6,7-dihydro-3H,5H-pyrrolo[2,3-f]benzimidazol-6-one Analogously to Example 5, 1.40 g. (4.0 mmole) 6-propylcarbonylamino-5-nitro-3-ethoxycarbonyl-3-methylindolin-2-one is suspended in 140 ml. ethanol and hydrogenated in the presence of 0.1 g. 10% palladium on charcoal at normal pressure and ambient temperature. After 270 ml. of hydrogen have been taken up, the catalyst is filtered off with suction and the filtrate is evaporated to dryness. The residue is stirred for 1 hour at 60° C. in 10 ml. glacial acetic acid, the glacial acetic acid is distilled off and the residue is taken up in water and neutralised with 2N aqueous sodium hydroxide solution. The mixture is shaken out three times with dichloromethane and the combined dichloromethane phases are dried over anhydrous sodium sulphate, filtered and the filtrate evaporated to dryness. After crystallisation of the residue from isopropanol, there is obtained 0.4 g. (33% of theory) of the title compound; m.p. 258°–261° C.

EXAMPLE 11

7,7-Dimethyl-2-(isopropenyl)-6,7-dihydro-3H,5H-pyrrolo[2,3-f]benzimidazol-6-one 3.0 g. (15.7 mmole) 5,6-diamino-3,3-dimethylindolin-2-one and 1.37 g. (15.9 mmole) methacrylic acid are heated for 30 minutes at 200° C. in 28 g. polyphosphoric acid. Thereafter, the reaction mixture is mixed with 40 ml. ice water. The brown suspension obtained is adjusted, while cooling with ice, to pH 8 with 45 ml. concentrated aqueous ammonia solution. The substance is filtered off with suction and washed with a little water. There are obtained 3.74 g. of crude product which are dissolved in 5 ml. dimethyl sulphoxide, diluted with 15 ml. methanol and purified over a silica gel column (7.50 g. gel; elution agent: dichloromethane/methanol 10:1 v/v). There is obtained 0.6 g. (14% of theory) of the title compound; m.p. 270°–273° C.

EXAMPLE 12

2-(1-Propenyl)-7,7-dimethyl-6,7-dihydro-3H,5H-pyrrolo[2,3-f]benzimidazol-6-one

Analogously to Example 11, 0.95 g. 5,6-diamino-3,3-dimethylindolin-2-one and 0.43 g. crotonic acid are heated with 10 ml. polyphosphoric acid for 30 minutes at 170° C. (bath temperature). The cooled reaction mixture is dissolved in 40 ml. water and neutralised with concentrated aqueous ammonia solution. Insoluble material is filtered off with suction, washed with water and dissolved in 100 ml. hot ethanol. After treatment with active charcoal, the hot filtrate is evaporated in a vacuum and the evaporation residue is triturated with diethyl ether. There is thus obtained 0.7 g. of the title compound which contains 0.5 mole of water per mole of substance; m.p. 252°–254° C.

EXAMPLE 13

2-n-Hexyl-7,7-dimethyl-6,7-dihydro-3H,5H-pyrrolo[2,3-f]benzimidazol-6-one

Analogously to Example 11, from 0.48 g. 5,6-diamino-3,3-dimethylindolin-2-one and 0.36 g. oenanthic acid, after heating with 4.5 g. polyphosphoric acid for 30 minutes at a bath temperature of 200° C., there is obtained 0.7 g. of crude product which is dissolved in 35 ml. ethanol, treated with active charcoal, filtered and the clear filtrate evaporated in a vacuum. The evaporation residue, after trituration with diethyl ether, gives 0.37 g. of the title compound in the form of the monohydrate; m.p. 233°–234° C.

EXAMPLE 14

7,7-Dimethyl-2-(1-cyclopenten-1-yl)-6,7-dihydro-3H,5H-pyrrolo[2,3-f]benzimidazol-6-one Analogously to Example 11, a mixture of 0.48 g. 5,6-diamino-3,3-dimethylindolin-2-one and 0.31 g. (1-cyclopenten-1-yl)-carboxylic acid is well stirred up with 4.5 g. warm polyphosphoric acid and then stirred for 30 minutes in a bath with a temperature of 200° C. After cooling, the reaction mixture is triturated with ice water, adjusted to pH 7–8 with concentrated aqueous ammonia solution and insoluble material is filtered off with suction, washed with water and dried, 0.51 g. of crude product thereby being obtained. This is repeatedly triturated with 6 ml. amounts of methanol, 0.25 g. of substance thereby remaining undissolved. This product is triturated three times with 6 ml. amounts of a mixture of methylene chloride/methanol (1:1 v/v), 0.14 g. of the desired title compound thereby being obtained which, per mole, still contains ⅔ mole methanol and 1 mole water; m.p. 233°–235° C.

A further 0.1 g. of the desired product is obtained from the evaporated methanol filtrate after analogous purification.

EXAMPLE 15

2-Cyclopropyl-7,7-dimethyl-6,7-dihydro-3H,5H-pyrrolo[2,3-f]benzimidazol-6-one

Analogously to Example 11, from 0.95 g. 5,6-diamino-3,3-dimethylindolin-2-one and 0.45 g. cyclopropane-carboxylic acid, there is obtained, after heating with 10 g. polyphosphoric acid for 1 hour at 150° C., 1.18 g. of crude product which is repeatedly boiled with ethanol. From the combined ethanol extracts, after treatment with active charcoal, evaporation of the hot, clear filtrate in a vacuum and trituration of the evaporation residue with diethyl ether, there is obtained 0.52 g. of the title compound which contains 0.75 mole water per mole of product; m.p. 266°–268° C.

EXAMPLE 16

2-(1,1-Dimethylethyl)-7,7-dimethyl-6,7-dihydro-3H,5H-pyrrolo[2,3-f]benzimidazol-6-one Analogously to Example 11, 0.286 g. 5,6-diamino-3,3-dimethylindolin-2-one and 0.18 g. pivalic acid are heated with 3 g. polyphosphoric acid in a pre-heated bath for 30 minutes at 200° C. A further 0.18 g. pivalic acid are then added thereto and further heated for 30 minutes at 200° C. This procedure is repeated three times so that, in all, 0.9 g. pivalic acid are used with a total reaction time of 2.5 hours. After cooling, the mixture is dissolved in about 9 ml. water and adjusted to about pH 7 to 8 with concentrated aqueous ammonia solution. The precipitate obtained is filtered off with suction and washed with water to give 0.28 g. of the title compound; m.p. >300° C. For further purification, it is dissolved in a little hot ethanol, the turbid solution is treated with charcoal, the hot clear filtrate is evaporated in a vacuum and the evaporation residue is triturated with diethyl ether. One mole of the title compound thus obtained contains 1 mole of water; m.p. >300° C.

EXAMPLE 17

7,7-Dimethyl-2-hydroxy-6,7-dihydro-3H,5H-pyrrolo[2,3-f]benzimidazol-6-one

Into a solution of 4.00 g. (0.021 mole) 5,6-diamino-3,3-dimethylindolin-2-one in 60 ml. 2N hydrochloric acid is passed phosgene at ambient temperature for 1 hour. Thereafter, nitrogen is passed through the solution for 10 minutes and the solution then left to stand for 15 hours. The precipitate is filtered off and crystallised from methanol. There are obtained 2.80 g. (62% of theory) of the title compound; m.p. >300° C.

EXAMPLE 18

Analogously to Example 17, from 4.80 g. (0.019 mole) 5,6-diamino-3-methylindolin-2-one, there are obtained 3.00 g. (77% of theory) 7-methyl-2-hydroxy-6,7-dihydro-3H,5H-pyrrolo[2,3-f]benzimidazol-6-one which, after crystallisation from methanol, has a melting point of >300° C.

EXAMPLE 19

Analogously to Example 17, from 2.50 g. (0.013 mole) 5,6-diamino-3-ethylindolin-2-one, there is obtained 1.80 g. (64% of theory) 7-ethyl-2-hydroxy-6,7-dihydro-3H,5H-pyrrolo[2,3-f]benzimidazol-6-one which, after crystallisation from pyridine, has a melting point of >300° C.

EXAMPLE 20

Analogously to Example 17, from 12.0 g. (0.063 mole) 5,6-diamino-3,3-dimethylindolin-2-one and 25 ml. thiophosgene, there are obtained 2.75 g. (19% of theory) 7,7-dimethyl-2-mercapto-6,7-dihydro-3H,5H-pyrrolo[2,3-f]benzimidazol-6-one with a melting point of >300° C. after purification over a silica gel column with dichloromethane/methanol (7:3 v/v) as elution agent and subsequent crystallisation from methanol.

EXAMPLE 21

1,7,7-Trimethyl-2-hydroxy-6,7-dihydro-5H-pyrrolo[2,3-f]benzimidazol-6-one 9.8 g. 1,1′-Carbonyldiimidazole are added to 6.1 g. 6-amino-5-methylamino-3,3-dimethylindolin-2-one in 250 ml. dioxan and the reaction mixture is heated under reflux for 2 hours. The solution is evaporated to dryness in a vacuum and the reddish oil remaining behind is boiled under reflux for 2 hours with 20% aqueous hydrochloric acid. The mixture is cooled to ambient temperature and neutralised with aqueous ammonia solution, while cooling with ice. The precipitate is filtered off with suction and recrystallised from methanol. There are obtained 2.0 g. of the title compound; m.p. 364°–367° C.

EXAMPLE 22

7,7-Dimethyl-2-hydroxy-6,7-dihydro-3H,5H-pyrrolo[2,3-f]benzoxazol-6-one 2.1 g. 5-Hydroxy-6-nitro-3,3-dimethylindolin-2-one are hydrogenated in a mixture of 50 ml. dioxan and 50 ml. methanol in the presence of 0.4 g. 10% palladium on charcoal. After 700 ml. of hydrogen have been taken up, the catalyst is filtered off with suction and the filtrate is evaporated to dryness in a vacuum. The dark residue (1.8 g.) is further reacted immediately without further purification.

The residue is dissolved in 50 ml. dioxan and 2.5 g. 1,1'-carbonyldiimidazole are added thereto. After heating under reflux for 3 hours, the solvent is removed in a vacuum and the residue is purified by column chromatography using 800 ml. silical gel and the elution agent dichloromethane/methanol (15:1 v/v). The appropriate fractions are evaporated and the residue is digested with dichloromethane and filtered off with suction. There is obtained 1.6 g. of colourless crystals which are recrystallised from methyl ethyl ketone to give 1.05 g. of the title compound in the form of colourless crystals; m.p. 297°–299° C.

EXAMPLE 23

7,7-Dimethyl-2-amino-6,7-dihydro-3H,5H-pyrrolo[2,3-f]benzimidazol-6-one 3.00 g. (0.016 mole) 5,6-diamino-3,3-dimethylindolin-2-one are suspended in 100 ml. ethanol and mixed at ambient temperature with 1.82 g. (0.017 mole) cyanogen bromide and stirred for 2 hours. The solvent is removed in a vacuum and the residue is dissolved in ethanol, treated with active charcoal and the product precipitated out by the addition of acetone. The product is crystallised from acetone and a little ethanol to give 1.05 g. (22% of theory) of the title compound in the form of the hydrobromide; m.p. 300°–305° C.

EXAMPLE 24

2-(4-Pyridylcarbonylamino)-7,7-dimethyl-6,7-dihydro-3H,5H-pyrrolo[2,3-f]benzimidazol-6-one 2.7 g. (9.1 mmole) of the compound prepared in Example 23 and 3.8 ml. triethylamine in 50 ml. pyridine are mixed portionwise at 0° C. with 1.62 g. (9.1 mmole) isonicotinic acid chloride hydrochloride. The reaction mixture is heated for 5 hours to 50° C., the pyridine is distilled off and the residue is digested with water. After crystallisation from ethanol, there is obtained 1.5 g. of the title compound; m.p. >300° C.

EXAMPLE 25

7,7-Dimethyl-2-methylthio-6,7-dihydro-3H,5H-pyrrolo-[2,3-f]benzimidazol-6-one 1.35 g. (5.79 mmole) of the compound prepared in Example 20 and 0.8 g. potassium carbonate are suspended in 120 ml. acetone. After 20 minutes, 0.4 ml. methyl iodide are added dropwise thereto, with ice cooling. After 40 hours at ambient temperature, the solvent is removed in a vacuum and the residue is digested with water. After purification over a silica gel column (elution agent: dichloromethane/methanol 7:3 v/v) and crystallisation from methanol, there is obtained 0.7 g. (49% of theory) of the title compound; m.p. 248°–250° C.

EXAMPLE 26

2-(2-Ethoxycarbonylethyl)-7,7-dimethyl-6,7-dihydro-3H,5H-pyrrolo[2,3-f]benzimidazol-6-one 0.41 g. of the compound prepared in Example 4, which contains 1.6 mole of water per mole of compound, is boiled under reflux with 18 ml. ethanol saturated with gaseous hydrogen chloride and then evaporated in a vacuum. The evaporation residue is dissolved in 15 ml. water, repeatedly extracted with diethyl ether, the aqueous phase is neutralised with sodium hydrogen carbonate, extracted several times with ethyl acetate, the combined ethyl acetate extracts are considerably evaporated in a vacuum and the crystallisate obtained is filtered off with suction, 0.32 g. of the title compound being obtained; m.p. 194°–196° C.

EXAMPLE 27

2-Propyl-7-methyl-6,7-dihydro-3H,5H-pyrrolo[2,3-f]benzimidazol-6-one 1.50 g. (4.9 mmole) of the compound prepared in Example 10 is stirred in 30 ml. 60% sulphuric acid for 1 hour at 60° C. bath temperature, then poured on to ice, neutralised with 2N aqueous ammonia solution and the precipitated product is filtered off with suction and the residue crystallised from ethyl acetate/methanol. There is obtained 0.70 g. (62% of theory) of the title compound; m.p. 235°–238° C.

Pharmaceutical Activity

The following experiment demonstrates the pharmaceutical activity of compound (I) of the invention:

Male Sprague-Dawley rats weighing between 350 and 450 g were narcotized by intraperitoneal injection of a barbiturate and fitted with instrumentation for the examinations as follows:

A pressure measuring catheter (Miller Mikrotip/-diameter 0.5 mm) was inserted through the arteria carotis dextra into the left ventricle. The pressure inside the left ventricle was continually registered through this catheter. The signal from this Mikrotip was electronically differentiated and $(dp/dt)_{60}$—the slope of the pressure-time curve at a pressure of 60 mmHg—was taken as a measure for the inotropy.

A polypropylene catheter was bound in a vena jugularis for the intravenous injection of the test substances.

A further polypropylene catheter was inserted through an arteria femoralis into the abdominal aorta for the direct measurement of the arterial blood pressure.

The ECG was traced with subcutaneous insertion electrodes.

During the preparation of the animal and during the entire test period the rate were fixed on an electrically heated and thermosated operating table.

Procedure

The test substances were always introduced by intravenous injection, with an injection volume, per injection, of 1 ml/kg body weight. In intervals of 10 min each, doses increasing from 0.01 to 30 mg of the test substances were intravenously injected. In this way dose effect curves for the measured parameters for the investigated substances were obtained.

From the measured data, using a regression calculation, equipotent doses for the positively inotropic effect $(dp/dt)_{60}$ were calculated. In addition, as criterion for the effectiveness of the substances, the maximum effect obtained maximal increase of $(dp/dt)_{60}$ and its corresponding dose were determined. The table that follows shows the equipotent doses ($DE_{1,5}$ = the dose in mg/kg that leads to an increase of $(dp/dt)_{60}$ of 1.5 mHg/sec) and the maximal effectiveness ($W_{max}$ = the maximal increase of $(dp/dt)_{60}$.

| Substance from Exp. | $ED_{1,5}$ mHg/sec [mg/kg i.v.] | $W_{max}$ [mHg/sec] | [mg/kg i.v.] |
| --- | --- | --- | --- |
| 1 | 0,19 | 3,2 | 3,0 |
| 2 | 1,0 | 2,1 | 3,0 |
| 6 | 0,17 | 2,5 | 1,0 |
| 7 | 0,13 | 2,3 | 3,0 |
| 8 | 0,48 | 3,5 | 10,0 |
| 17 | 0,13 | 3,0 | 1,0 |
| 5 | 0,21 | 2,3 | 1,0 |
| 20 | 0,55 | 3,5 | 3,0 |
| 25 | 1,01 | 2,3 | 3,0 |

It will be understood that the specification and examples are illustrative but not limitative of the present invention and that other embodiments within the spirit and scope of the invention will suggest themselves to those skilled in the art.

What is claimed is:

1. A compound of the formula:

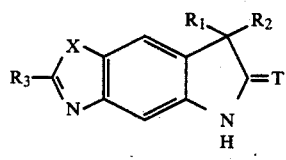

wherein $R_1$ is hydrogen, $C_1-C_6$ alkyl, $C_2-C_6$ alkenyl or $C_3-C_7$ cycloalkyl;

$R_2$ is hydrogen, cyano, $C_1-C_6$ alkyl, $C_2-C_6$ alkenyl, or a carbonyl group substituted by hydroxyl, $C_1-C_6$ alkyl, $C_1-C_6$ alkoxy, amino, $C_1-C_6$ alkylamino, $C_2-C_{12}$ dialkylamino or hydrazino, or $R_2$ and $R_1$ together with the carbon to which they are attached form a $C_3-C_7$ cycloalkyl ring, or $R_1$ and $R_2$ together form $C_3-C_7$ alkylidene or $C_3-C_7$ cycloalkylidene, T is oxlygen or sulphur or an $NR_4$ group wherein $R_4$ is hydrogen or a $C_1-C_6$ alkyl;

$R_3$ is hydrogen, $C_1-C_6$ alkyl, hydroxyl, amino or mercapto, $C_1-C_6$ alkylthio, pyridylcarbonylamino, $C_1-C_6$ alkylcarbonylamino, $C_3-C_7$ cycloalkyl, $C_2-C_6$ alkenyl, $C_3-C_7$ cycloalkenyl, $C_2-C_6$ alkynyl, $C_1-C_6$ haloalkyl, $C_1-C_6$-alkoxy-$C_1-C_6$-alkyl, carboxy-$C_1-C_6$-alkyl or $C_1-C_6$-alkoxycarbonyl-$C_1-C_6$-alkyl and X is an oxygen or sulphur atom or an $>NR_5$ group, wherein $R_5$ is hydrogen or an $C_1-C_6$ alkyl;

a tautomer thereof or a physiologically acceptable salt thereof with an inorganic or organic acid.

2. The compound of claim 1 wherein $R_1$ and $R_2$ are the same and are methyl or ethyl or $R_1$ and $R_2$ are different and are hydrogen, methyl, ethyl, isopropyl, cyclopentyl, cyano, acetyl, methoxycarbonyl, ethoxycarbonyl, aminocarbonyl or hydrazinocarbonyl groups or $R_1$ and $R_2$ form a spirocyclopentyl ring when $R_1$ and $R_2$ form a cycloalkyl ring with the carbon atom to which they are attached, $R_3$ is hydrogen, methyl, ethyl, propyl, isopropyl, butyl, tert.-butyl, pentyl, hexyl, propenyl, isopropenyl, cyclopropyl, cyclopentenyl, cyclohexyl, trifluoromethyl, hydroxyl, mercapto, methylthio, amino, acetylamino, pyridylcarbonylamino, carboxyethyl, ethoxycarbonylethyl or methoxymethyl radical, X is oxygen atom or $>NR_5$, in which $R_5$ is hydrogen or methyl, and T is oxygen, or a tautomer thereof or the physiologically acceptable salts thereof with an inorganic or organic acid.

3. The compound of claim 1 wherein $R_1$ is methyl or ethyl, $R_2$ is hydrogen, methyl, ethyl, methoxycarbonyl or ethoxycarbonyl or $R_1$ and $R_2$, together with the carbon atom to which they are attached, represent spirocyclopentyl or spirocyclohexyl, $R_3$ is hydrogen or a methyl, ethyl, propyl, hexyl, isopropyl, propenyl, isopropenyl, tert.-butyl, cyclopropyl, cyclohexyl, cyclopentenyl, trifluoromethyl, hydroxyl, mercapto, methylthio, amino, pyridylcarbonylamino, carboxyethyl, ethoxycarbonylethyl or methoxymethyl, X is oxygen, an imino group or an N-methylimino group and T is an oxygen atom or a tautomer thereof or a physiologically acceptable salt thereof with an inorganic or organic acid.

4. The compound of claim 1, wherein $R_1$ and $R_2$ are methyl or ethyl, X is oxygen, imino or N-methylimino and T is oxygen, or a tautomer thereof or a physiologically acceptable salt thereof with an inorganic or organic acid.

5. The compound of claim 1 wherein $R_1$ and $R_2$ are the same and are methyl or ethyl.

6. The compound of claim 1 wherein $R_1$ and $R_2$ are different.

7. The compound of claim 1 wherein $R_1$ and $R_2$ form a $C_5$ or $C_6$ spirocycloalkyl ring.

8. The compound of claim 1 wherein $R_1$ and $R_2$ form a spirocyclopentyl ring.

9. The compound of claim 1 designated 7,7-dimethyl-6,7-dihydro-3H,5H-pyrrolo[2,3-f]benzimidazol-6-one.

10. The compound of claim 1 designated 7,7-dimethyl-2-cyclohexyl-6,7-dihydro-3H,5H-pyrrolo[2,3-f]benzimidazol-6-one.

11. The compound of claim 1 designated 7,7-dimethyl-2-(2-propyl)-6,7-dihydro-3H,5H-pyrrolo[2,3-f]benzimidazol-6-one.

12. The compound of claim 1 designated 2-(1-propyl)-7,7-dimethyl-6,7-dihydro-3H,5H-pyrrolo[2,3-f]benzimidazol-6-one.

13. The compound of claim 1 designated 7,7-dimethyl-2-trifluoromethyl-6,7-dihydro-3H,5H-pyrrolo[2,3-f]benzimidazol-6-one.

14. The compound of claim 1 designated 2,7,7-trimethyl-6,7-dihydro-3H,5H-pyrrolo[2,3-f]benzimidazol-6-one.

15. The compound of claim 1 designated 7,7-dimethyl-2-hydroxy-6,7-dihydro-3H,5H-pyrrolo[2,3-f]benzimidazol-6-one.

16. The compound of claim 1 designated 7,7-dimethyl-2-mercapto-6,7-dihydro-3H,5H-pyrrolo[2,3-f]benzimidazol-6-one.

17. The compound of claim 1 designated 7,7-dimethyl-2-methylthio-6,7-dihydro-3H,5H-pyrrolo[2,3-f]benzimidazol-6-one.

18. A pharmaceutical composition containing at least one compound of claim 1 for the prophylaxis or treatment of heart or circulatory diseases in a mammal, in an amount sufficient to exhibit at least one physiological effect selected from the group of a positive inotropic effect to increase the power of the heart, a blood pressure-lowering action, an influence on thrombocyte aggregation and an improvement of the micro-circulation, said compound being present in a physiologically acceptable carrier.

19. The pharmaceutical composition of claim 18 wherein said compound is
7,7-dimethyl-6,7-dihydro-3H,5H-pyrrolo[2,3-f]benzimidazol-6-one,
7,7-dimethyl-2-cyclohexyl-6,7-dihydro-3H,5H-pyrrolo[2,3-f]benzimidazol-6-one,
7,7-dimethyl-2-(2-propyl)-6,7-dihydro-3H,5H-pyrrolo[2,3-f]benzimidazol-6-one,
2-(1-propyl)-7,7-dimethyl-6,7-dihydro-3H,5H-pyrrolo[2,3-f]benzimidazol-6-one,
7,7-dimethyl-2-trifluoromethyl-6,7-dihydro-3H,5H-pyrrolo[2,3-f]benzimidazol-6-one,
2,7,7-trimethyl-6,7-dihydro-3H,5H-pyrrolo[2,3-f]benzimidazol-6-one,
7,7-dimethyl-2-hydroxy-6,7-dihydro-3H,5H-pyrrolo[2,3-f]benzimidazol-6-one,
7,7-dimethyl-2-mercapto-6,7-dihydro-3H,5H-pyrrolo[2,3-f]benzimidazol-6-one, or
7,7-dimethyl-2-methylthio-6,7-dihydro-3H,5H-pyrrolo[2,3-f]benzimidazol-6-one.

20. A method of treating heart or circulatory diseases in a mammal comprising administering at least one of the compounds of claim 1 in an amount sufficient to exhibit at least one physiological effect selected from the group of a positive inotropic effect to increase the power of the heart, a blood pressure-lowering action, an influence on thrombocyte aggregation and an improvement of the micro-circulation.

21. The method of claim 20, wherein 0.1 to 500 mg per 75 kg body weight, are administered per day.

22. A method for the treatment or prophylaxis of heart or circulatory diseases in a mammal comprising administering at least one of the compounds of claim 1 in an amount sufficient to exhibit at least one physiological effect selected from the group of a positive inotropic effect to increase the power of the heart, a blood pressure-lowering action, an influence on thrombocyte aggregation and an improvement of the micro-circulation.

* * * * *

UNITED STATES PATENT AND TRADEMARK OFFICE
CERTIFICATE OF CORRECTION

PATENT NO. : 4,730,003

DATED : March 8, 1988

INVENTOR(S) : von der Saal et al.

It is certified that error appears in the above-identified patent and that said Letters Patent is hereby corrected as shown below:

Column 14, line 9: delete "[cyclopentone-" and insert -- [cyclopentane- --.

Column 21, line 44, Claim 1 : delete "oxlygen" and insert -- oxygen --.

Signed and Sealed this

Third Day of January, 1989

Attest:

DONALD J. QUIGG

Attesting Officer

Commissioner of Patents and Trademarks